(12) United States Patent
Kjaer

(10) Patent No.: US 11,079,317 B2
(45) Date of Patent: *Aug. 3, 2021

(54) OPTICAL SENSOR FOR DETECTION OF FREE HEMOGLOBIN IN A WHOLE BLOOD SAMPLE

(71) Applicant: Radiometer Medical ApS, Brønshøj (DK)

(72) Inventor: Thomas Kjaer, Smoerum (DK)

(73) Assignee: RADIOMETER MEDICAL APS, Brønshøj (DK)

( * ) Notice: Subject to any disclaimer, the term of this patent is extended or adjusted under 35 U.S.C. 154(b) by 404 days.

This patent is subject to a terminal disclaimer.

(21) Appl. No.: 15/776,237

(22) PCT Filed: Nov. 17, 2016

(86) PCT No.: PCT/EP2016/077990
§ 371 (c)(1),
(2) Date: May 15, 2018

(87) PCT Pub. No.: WO2017/085180
PCT Pub. Date: May 26, 2017

(65) Prior Publication Data
US 2020/0256845 A1 Aug. 13, 2020

(30) Foreign Application Priority Data

Nov. 18, 2015 (DK) .......................... PA 2015 00740

(51) Int. Cl.
*G01N 21/31* (2006.01)
*G01N 33/49* (2006.01)
(Continued)

(52) U.S. Cl.
CPC ........ *G01N 21/31* (2013.01); *B01L 3/502715* (2013.01); *G01N 33/49* (2013.01);
(Continued)

(58) Field of Classification Search
None
See application file for complete search history.

(56) References Cited

U.S. PATENT DOCUMENTS

| 5,418,143 A | * | 5/1995 | Zweig | ....................... C12Q 1/56 422/401 |
| 5,580,744 A | * | 12/1996 | Zweig | ....................... C12Q 1/56 422/401 |

(Continued)

FOREIGN PATENT DOCUMENTS

| CA | 2 742 975 A1 | 6/2010 |
| CN | 1934444 A | 3/2007 |

(Continued)

OTHER PUBLICATIONS

Archibong, Edikan et al., "Optofluidic spectroscopy integrated on optical fiber platform," Sensing and Bio-Sensing Research, vol. 3, pp. 1-6 (2015).

(Continued)

*Primary Examiner* — Shawn Decenzo
(74) *Attorney, Agent, or Firm* — Finnegan, Henderson, Farabow, Garrett & Dunner, LLP

(57) ABSTRACT

Sensor for the optical detection of free hemoglobin (96) in a whole blood sample (99), the sensor comprising a translucent slab (2) with a front side (3) and a back side (4) facing away from the front side (3), wherein the front side (3) is adapted for being contacted with a whole blood sample (99); a reflective layer (5) at the front side (3) of the translucent slab (2), the reflective layer (5) being adapted to reflect light reaching the reflective layer (5) from the translucent slab (2); an optical probing device comprising a light source (10) and a detector (20), wherein the light source (10) is adapted to illuminate at least pores in the translucent slab, wherein the detector (20) is arranged to receive light (21) emerging from the pores (6) in response to an illumination (11) by the light (Continued)

source (10), and wherein the detector (20) is adapted to generate a signal representative of the detected light. The translucent slab (2) is provided with dead-end pores (6) extending from the front side (3) into the translucent slab (2) in a direction towards the backside (4). Each of the pores (6) has a respective opening (7) in the front side (3) of the translucent slab (2) penetrating the reflecting layer (5). A cross-sectional dimension of the openings (7) of the pores (6) is dimensioned so as to prevent red blood cells (98) from entering the pores (6), while allowing free hemoglobin (96) to enter the pores (6).

17 Claims, 6 Drawing Sheets

(51) Int. Cl.

| | | |
|---|---|---|
| *B01L 3/00* | (2006.01) | |
| *G01N 33/72* | (2006.01) | |
| *G01N 21/03* | (2006.01) | |
| *A61B 5/00* | (2006.01) | |
| *G01N 15/00* | (2006.01) | |
| *A61B 5/15* | (2006.01) | |

(52) U.S. Cl.
CPC ......... *G01N 33/491* (2013.01); *G01N 33/728* (2013.01); *A61B 5/0075* (2013.01); *A61B 5/15* (2013.01); *B01L 3/502753* (2013.01); *G01N 2015/0065* (2013.01); *G01N 2021/0357* (2013.01); *G01N 2201/061* (2013.01)

(56) References Cited

U.S. PATENT DOCUMENTS

| | | | | |
|---|---|---|---|---|
| 6,040,191 | A * | 3/2000 | Grow | G01N 21/65 436/172 |
| 7,959,791 | B2 * | 6/2011 | Kjaer | C12Q 1/002 205/778 |
| 10,663,395 | B2 * | 5/2020 | Kjaer | G01N 33/491 |
| 2004/0156037 | A1 | 8/2004 | Mawhirt et al. | |
| 2004/0201835 | A1 * | 10/2004 | Coates | G01N 21/552 356/73 |
| 2005/0191620 | A1 | 9/2005 | McDevitt et al. | |
| 2006/0257854 | A1 | 11/2006 | McDevitt et al. | |
| 2006/0275857 | A1 * | 12/2006 | Kjaer | C12Q 1/002 435/23 |
| 2009/0098467 | A1 | 4/2009 | Lowe et al. | |
| 2012/0086021 | A1 * | 4/2012 | Wang | G01N 21/658 257/84 |
| 2012/0194813 | A1 * | 8/2012 | Tzeng | G01N 21/658 356/301 |
| 2012/0238840 | A1 * | 9/2012 | Hashimoto | A61B 5/1455 600/310 |
| 2013/0040333 | A1 | 2/2013 | Karlsson | |
| 2013/0114076 | A1 * | 5/2013 | Schleipen | A61B 5/0059 356/246 |
| 2013/0184188 | A1 | 7/2013 | Ewart et al. | |
| 2014/0118745 | A1 * | 5/2014 | Neijzen | G01N 21/552 356/432 |
| 2014/0193892 | A1 | 7/2014 | Mohan et al. | |
| 2014/0211206 | A1 * | 7/2014 | Wang | G01N 21/658 356/300 |
| 2014/0327909 | A1 * | 11/2014 | Kall | G01N 21/4133 356/327 |
| 2014/0329268 | A1 | 11/2014 | Karlsson | |
| 2015/0131092 | A1 * | 5/2015 | Sakagami | G01N 21/658 356/301 |
| 2015/0168371 | A1 * | 6/2015 | Babson | G01N 33/49 356/40 |
| 2015/0293016 | A1 * | 10/2015 | Perkins | C25D 5/10 356/70 |
| 2017/0241899 | A1 * | 8/2017 | Jones | G01N 21/314 |
| 2020/0256845 | A1 * | 8/2020 | Kjaer | G01N 21/31 |

FOREIGN PATENT DOCUMENTS

| | | |
|---|---|---|
| CN | 1975377 A | 6/2007 |
| CN | 104136911 A | 11/2014 |
| DE | 102 23 450 A1 | 12/2003 |
| DE | 10 2013 018 284 A1 | 4/2015 |
| EP | 1 256 797 A2 | 11/2002 |
| EP | 2 444 803 A1 | 4/2012 |
| GB | 2 090 659 A | 7/1982 |
| JP | 59-214765 A | 12/1984 |
| JP | 2001-514744 A | 9/2001 |
| JP | 2002-538458 A | 11/2002 |
| JP | 2003-004733 A | 1/2003 |
| JP | 2004-532388 A | 10/2004 |
| JP | 2006-518462 A | 8/2006 |
| JP | 2007-523321 A | 8/2007 |
| JP | 2010-503002 A | 1/2010 |
| JP | 2010-204011 A | 9/2010 |
| JP | 2012-522249 A | 9/2012 |
| JP | 2013-164372 | 8/2013 |
| WO | WO 2005/059524 A1 | 6/2005 |
| WO | WO 2005/062986 A2 | 7/2005 |
| WO | WO 2014/024066 A1 | 2/2014 |
| WO | WO 2014/105070 A1 | 7/2014 |
| WO | WO 2015/010709 | 1/2015 |
| WO | WO 2015/191450 A1 | 12/2015 |

OTHER PUBLICATIONS

Crowley, Timothy A. et al., "Isolation of plasma from whole blood using planar microfilters for lab-on-a-chip applications," Lab on a Chip, vol. 5, No. 9, pp. 922-929 (2005).

Miney, Paul G. et al., "A New Optically Reflective Thin Layer Electrode (ORTLE) Window: Gold on a Thin Porous Alumina Film Used to Observe the Onset of Water Reduction," Electroanalysis, vol. 16, No. 1-2, pp. 113-119 (2004).

International Search Report for International Application No. PCT/EP2016/077990, dated Jan. 30, 2017.

Written Opinion of the International Search Authority for International Application No. PCT/EP2016/077990.

* cited by examiner

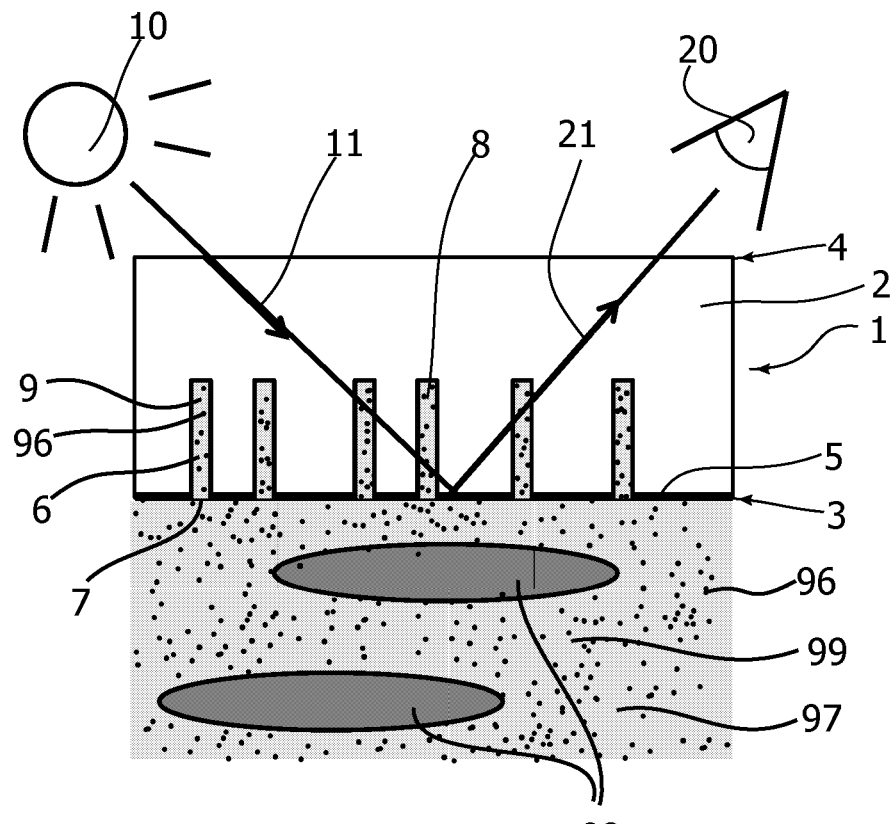
Fig. 1
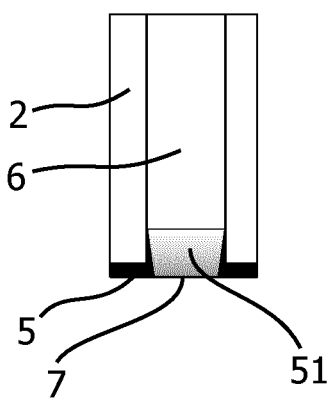
Fig. 2
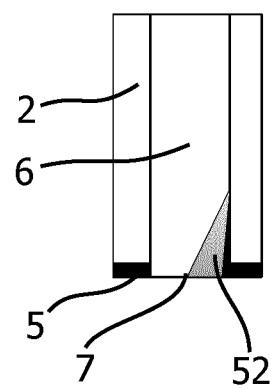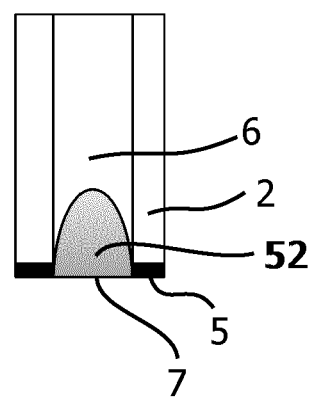
Fig. 3a    Fig. 3b

OPTICAL SENSOR FOR DETECTION OF FREE HEMOGLOBIN IN A WHOLE BLOOD SAMPLE

This application is a national stage filing under 35 U.S.C. § 371 of International Application No. PCT/EP2016/077990, filed on Nov. 17, 2016, which claims priority of Danish Patent Application No. PA 2015 00740, filed Nov. 18, 2015. The contents of these applications are each incorporated herein by reference.

The present invention relates in one aspect to a sensor for the optical detection of free hemoglobin in a whole blood sample. In a further aspect, the present invention relates to a system for analyzing blood comprising a sensor for the optical detection of free hemoglobin in a whole blood sample. According to a further aspect of the invention, a porous mirror for use in the optical detection of free hemoglobin in a whole blood sample is provided. According to a yet further aspect of the invention, a method is provided for optically detecting free hemoglobin in whole blood. Further, a method for analyzing whole blood comprises optically detecting free hemoglobin.

According to a broader aspect, the present invention relates to a sensor for the optical detection of substances in the plasma fraction of a whole blood sample. In a further aspect, the present invention relates to a system for analyzing blood comprising a sensor for the optical detection of substances in the plasma fraction of a whole blood sample. According to a further aspect of the invention, a porous mirror for use in the optical detection of substances in the plasma fraction of a whole blood sample is provided. According to a yet further aspect of the invention, a method is provided for optically detecting substances in the plasma fraction of whole blood. Further, a method for analyzing a whole blood sample comprises optically detecting substances in the plasma fraction of the whole blood sample.

BACKGROUND OF THE INVENTION

Hemolysis is a frequently encountered phenomenon in whole blood, serum, or plasma samples and may compromise a laboratory's test parameters for blood analysis. The term "hemolysis" refers to the rupture of red blood cells, causing the release of the hemoglobin and other internal components into the surrounding fluid. Hemolysis may be caused by intrinsic factors that are related to a condition of the patient, or caused by extrinsic factors that are unrelated to the patient's condition. In vivo hemolysis may be due to pathological conditions such as autoimmune hemolytic anemia or transfusion reaction. In vitro hemolysis may be due to improper specimen sample collection, specimen sample processing or specimen sample transport. In particular, hemolysis may be caused by a high pressure drop and high shear or elongation rate, which may e.g. occur during filtration processes, when the sample is passed through a porous filter medium. Other important factors for hemolysis are bacterial contamination, pressure, temperature, osmotic environment, pH value, contact with surfaces, frictional forces, or blood age and storage time of the unseparated whole blood sample. Pronounced hemolysis can be visually detected as a red coloring in the plasma.

Hemolysis affects the measurement of a number of blood parameters as determined in blood parameter analyzers. Disregarding a level of free hemoglobin in the blood sample may thus mislead an unaware person and as a result provide a wrong diagnosis based on the affected blood parameter value. However, reliably determining a level of free hemoglobin present in the plasma fraction of a whole blood sample hitherto involved a complex process requiring separation of the plasma fraction from the cellular components and a subsequent analysis of the separated plasma fraction. Such a procedure is time consuming and may be prohibitive in cases where only very small samples are available at a time, such as in neonatal care with a continued monitoring of blood parameters in the infant. Other approaches for measuring components present in the plasma fraction in whole blood involve the separation of a plasma fraction from cellular components by microfiltration techniques in e.g. a microfluidic device, prior to analysis of the plasma fraction in a dedicated measurement in the microfluidic device. For example, a recent scientific article by Archibong et al. and published in Sensing and Bio-Sensing Research 3 (2015), p. 1-6, discloses a miniature measuring chamber for optically analyzing a plasma fraction that has been separated from a whole blood sample. In this type of device, a miniature microfluidic chamber is attached to the interface of an optical fiber. The bottom of the microfluidic chamber consists of a porous membrane that allows fluids and chemical compounds to flow inside the device, while at the same time filtering out undesired particles. The inside of the microfluidic chamber receiving the filtrate can be optically probed through a single optical fiber in normal-incidence reflection geometry.

However, such filtration-based approaches have several disadvantages when used for analyzing whole blood samples. Filtration devices inherently rely on a fluid flow of at least the filtrate through the pores of the filter from a sample feed to a filtrate analysis/measurement chamber. In through-flow geometries, the retentate (here the red blood cells) gradually clogs the filtration pores. In crossflow geometries, the retentate is lead along the surface of the filtering membrane, thereby reducing but not removing the problem with clogging, especially if the system is intended for repetitive use (more than 10-100 samples). Crossflow geometry also induces friction and shear interaction between the retentate and the surface of the filtering device. When analyzing whole blood samples, the corresponding pressure gradients, shear and flow patterns in such micro-filtration based devices tend to provoke hemolysis in vitro, thereby affecting the measurement of different substances, and in particular of free hemoglobin. Indeed, in some cases, the analysis of the components in the plasma fraction of a whole blood sample may thereby be rendered completely useless. Furthermore, the disclosed device is most useful as a disposable rather than for continued and repetitive use, since a complete washout of a sample after measurement may be difficult or at least very time-consuming and unreliable, at the further risk of cross-contamination between subsequent samples. In this particular type of device, additional challenges for obtaining quantitative results from the optical probing may arise, due to pressure-induced deformation of the filtration membrane resulting in a change of the optical path for probing the filtrate.

Therefore there is a need for an improved device and method for the detection of hemolysis by determining a level of free hemoglobin in a whole blood sample with a fast and reliable response. More generally, there is a need for an improved device and method for the detection of substances in the plasma fraction of a whole blood sample with a fast and reliable response.

Object of the present invention is to provide an improved detection overcoming at least some of the disadvantages of known sensors, systems and or methods for detecting substances in the plasma fraction of a whole blood sample, and in particular for detecting free hemoglobin in a whole blood sample.

SUMMARY OF THE INVENTION

A first aspect of the invention relates to a sensor for the optical detection of free hemoglobin in a whole blood sample, the sensor comprising a translucent slab with a front side and a back side facing away from the front side, wherein the front side is adapted for being contacted with a whole blood sample; a reflective layer at the front side of the translucent slab, the reflective layer being adapted to reflect light reaching the reflective layer from the translucent slab; and a light source and a detector configured for optically probing the translucent slab, wherein the light source is adapted to illuminate at least the pores, wherein the detector is arranged to receive light emerging from the pores in response to an illumination by the light source, and wherein the detector is adapted to generate a signal representative of the detected light; wherein the translucent slab is provided with dead-end pores extending from respective openings at the front side through the reflective mirror and into the translucent slab, wherein a cross-sectional dimension of the openings of the pores is dimensioned so as to prevent red blood cells from entering the pores, while allowing free hemoglobin to enter the pores.

The term "whole blood" refers to blood composed of blood plasma, and cellular components. The plasma represents about 50%-60% of the volume, and cellular components represent about 40%-50% of the volume. The cellular components are erythrocytes (red blood cells), leucocytes (white blood cells), and thrombocytes (platelets). Preferably, the term "whole blood" refers to whole blood of a human subject, but may also refer to whole blood of an animal. Erythrocytes constitute about 90%-99% of the total number of all blood cells. They are shaped as biconcave discs of about 7 µm in diameter with a thickness of about 2 µm in an un-deformed state. The erythrocytes are highly flexible, which allows them to pass through very narrow capillaries, reducing their diameter down to about 1.5 µm. One core component of erythrocytes is hemoglobin which binds oxygen for transport to the tissues, then releases oxygen and binds carbon dioxide to be delivered to the lungs as waste product. Hemoglobin is responsible for the red color of the erythrocytes and therefore of the blood in total. Leucocytes make up less than about 1% of the total number of all blood cells. They have a diameter of about 6 to about 20 µm. Leucocytes participate in the body's immune system e.g. against bacterial or viral invasion. Thrombocytes are the smallest blood cells with a length of about 2 to about 4 µm and a thickness of about 0.9 to about 1.3 µm. They are cell fragments that contain enzymes and other substances important to clotting. In particular, they form a temporary platelet plug that helps to seal breaks in blood vessels.

The terms "blood plasma" or "plasma" refer to the liquid part of the blood and lymphatic fluid, which makes up about half of the volume of blood (e.g. about 50%-60% by volume). Plasma is devoid of cells. It contains all coagulation factors, in particular fibrinogen and comprises about 90%-95% water, by volume. Plasma components include electrolytes, lipid metabolism substances, markers, e.g. for infections or tumors, enzymes, substrates, proteins and further molecular components.

The term "hemolysis" refers to the rupture of erythrocytes, e.g. due to chemical, thermal or mechanical influences, causing the release of the hemoglobin and other internal components into the surrounding fluid. The term "free hemoglobin" denotes hemoglobin in the plasma phase of the whole blood sample, i.e. hemoglobin in the blood that is not bound by or contained in red blood cells. The amount of free hemoglobin in a whole blood sample is an indication of the level of hemolysis in the whole blood sample. The sensor according to the present invention provides a technique that allows for selectively measuring the free hemoglobin content in the plasma phase of a whole blood sample. Based on the output of the detector, the whole blood sample, and any measurements of blood parameters obtained from it may then be corrected, flagged or discarded.

The term "translucent" refers to a material's property of allowing light to pass through. The term "transparent" refers to the property of a material of allowing light to pass through the material without being scattered. The term "transparent" is thus considered a sub-set to the term "translucent".

The core of the sensor is a porous mirror comprising a translucent slab and a reflecting layer applied to a front side of the translucent slab. The translucent slab contains small, dead-end pores extending from the front side, through the reflective layer into the translucent slab. The sensor uses a light source and a detector arranged to optically probe the content of the pores, and to generate a corresponding signal output representative of the free hemoglobin content in a whole blood sample.

Each of the small pores has an opening through which it can communicate with a sample space at the front side of the translucent slab. The pores thus penetrate the reflecting layer to allow for fluid communication between the pores and the sample space. The pores extend from the respective opening at the front side into the translucent slab in a direction towards the backside. The pores are "dead-end" meaning that the pores end within the translucent slab. The pores do not continue all the way through the translucent slab to the backside or to any common reservoir or recipient inside the slab. The pores are only in fluid communication with the sample space at the front side of the translucent slab. Note that in some embodiments the dead-end pores can be criss-crossing and at least some of the pores may thus be connected to each other forming an X-shape, a Y-shape, a V-shape, or similar interconnected shapes. Such a configuration is equally considered as dead-end, since the pores are only filled from the front side and no significant net mass transport passing through the pores occurs under operation, even if they cross each other. By appropriately dimensioning the opening of the pores at the front side it is possible to prevent red blood cells of a whole blood sample on the front side of the porous mirror from entering the pores, while allowing relevant components in the plasma of the whole blood sample to enter the pores, wherein relevant components are substances present in the plasma phase of the whole blood sample and that are to be measured/detected using the sensor. In particular, free hemoglobin is a relevant component.

Under operation, the front side of the translucent slab is contacted with a whole blood sample. The small pores in the translucent slab communicate with the whole blood sample through the openings in the front side. The pore openings are dimensioned to selectively extract a sub-sample of the plasma phase of the whole blood sample. No red blood cells can enter the pores through the openings on the front side of the translucent slab. As mentioned, the pores are dead-end, only communicating with the front side of the translucent slab, i.e. the sub-sample is extracted for optical probing inside the pores and after the measurement discharged again through the same openings in the front side of the translucent slab. The sub-sample volume corresponds to the total internal volume of the pores. No filtration and net mass transport of any filtrate occurs through the pore containing layer—neither into any common filtrate recipient nor to any filtrate outlet. The optical detection is then performed only on the sub-sample contained in the pores. The reflective layer optically separates the optical probing region in the translucent slab from the sample space containing the whole blood sample. By optically separating the probing region from the sample space, any contribution of the intact red blood cells of the whole blood sample to the probed signal can be effectively suppressed. The measurement is thus specific to the content of free hemoglobin in the whole blood sample.

The small, sub-sample with a representative content of the relevant components may be transferred to the pores in any suitable manner. However, care should be taken to not induce hemolysis by the transfer mechanism. The small, dead-end pores allow for a very efficient and fast extraction of the sub-sample for optical probing from the whole blood sample through the openings in the front side by means of capillary forces and/or diffusion.

In a typical operation mode, the front side surface of the translucent slab is contacted by a rinsing fluid prior to contacting the front side with a whole blood sample that is to be analyzed. Thereby, the pores are 'primed' with a prefill of a liquid that is compatible with a whole blood sample, and in particular a liquid that is compatible with the plasma phase, such as an aqueous solution commonly used for rinse, calibration and/or quality control purposes in blood analyzers. Typical rinse liquids used for e.g. wash-out in whole blood analyzer systems may be used as such a liquid. Rinse liquids are aqueous solutions comprising $K^+$, $Na^+$, $Cl^-$, $Ca^{2+}$, $O_2$, pH, $CO_2$, and $(HCO_3)^-$ in concentrations corresponding to human plasma. Non-limiting examples of suitable solutions commonly used for rinse, calibration and/or quality control purposes are given further below. When the whole blood sample is then brought in contact with the front side surface that is primed with a plasma compatible liquid, a representative sub-sample of components in the plasma phase of the whole blood sample is extracted and transferred in a very efficient and gentle manner by means of diffusion of the relevant components into the prefilled pore. In particular any concentration gradient in the content of free hemoglobin between the whole blood sample and the reference liquid in the pores drives a diffusive transfer, thereby producing in the pores a sub-sample with a free hemoglobin concentration representative of the free hemoglobin concentration in the whole blood sample.

In another operation mode, it may also be conceived to directly contact the front side of a dry sensor with a whole blood sample. Further preferably in this operation mode, an inside surface of the pores is hydrophilic, thereby extracting the sub-sample from the whole blood sample at the front side of the translucent slab into the pores by means of capillary forces. When operating a sensor in this mode calibration could occur either via batch calibration as sensors produced from the same batch of porous membrane material tend to have equal sensitivity (equal light absorption when measuring on identical samples using sensors produced from different pieces of porous membrane material from the same batch forming the translucent slab). Alternatively, the pores of the translucent slab can contain a calibration dye with absorption characteristics different from hemoglobin. The calibration dye is useful for normalizing/calibrating the optical probing signal, while being spectrally distinguishable from the substance in the plasma, e.g. free hemoglobin, to be detected/measured. Since the calibration dye will not be present in the actual sample, the calibrant dye will diffuse out of the sensor during the measurement, meanwhile free hemoglobin diffuses into the pores of the sensor. By optically probing the pores before and after acquiring the sample, a quantitative measure for the substance to be detected (e.g. hemoglobin) may be developed by a comparison of the calibration reference and sample substance signals.

The content of the pores can conveniently be probed optically from the back side of the translucent slab, or more generally, from the side of the reflective layer facing towards the translucent slab, wherein the reflective layer optically separates an optical probing region comprising the pores from the whole blood sample contacting the front side of the translucent slab. The reflective layer is adapted to reflect light reaching the reflective layer from the inside of the translucent slab, thereby preventing probing light from reaching and interacting with the whole blood sample at the front side of the mirror. The optical probing is thus selectively performed only on the sub-sample inside the pores.

Incident light is guided/directed to the optical probing region to ensure that the light traverses the pores and interacts with the sub-sample therein. Preferably, the probing light is sent into the probing region at an oblique incidence with respect to a surface normal on the plane of the reflective layer, to ensure that the light traverses the pores filled with the fluid to be probed, thereby ensuring a maximum of optical interaction path length.

Light emerging from the pores in response to the illumination has interacted with the sub-sample in the pores and thus carries information on the sub-sample. The emerging light and/or a signal representative of the emerging light may then be analyzed with respect to that information in order to develop a value representative of the free hemoglobin content in the whole blood sample. Analysis may include spectrally analyzing the emerging/detected light, and/or signal/data processing, e.g. for comparing the obtained signal with signals obtained on calibration/reference samples, for noise filtering, for applying corrections, and for removing artefacts.

In a particularly advantageous embodiment, it is the redish coloring of the plasma by free hemoglobin that is probed optically, e.g. by using spectrally resolved absorbance measurements, or by measuring the spectrally integrated absorbance over a predetermined bandwidth within a spectral range indicative of the presence of free hemoglobin in the liquid sub-sample, such as within a spectral range of wavelengths 380 nm-450 nm, such as within a spectral range of wavelengths 500 nm-600 nm, or at about 416 nm.

Further according to one embodiment of a sensor according to the invention, a cross-sectional dimension of the openings of the pores is about 1 µm or less, about 800 nm or less, preferably about 500 nm or less, or even about 400 nm or less, and/or a length of the pores in an axial direction along the pores is less than 100 µm, less than 50 µm, preferably less than 30 µm, or about 25 µm.

By using pores having an opening in the plane of the front side of the translucent slab with a maximum cross-sectional dimension of about 1 µm or less, or preferably in the submicron range, such as about 800 nm or less, such as about 500 nm or less, or even about 400 nm or less, any cellular components including erythrocytes, leucocytes, and thrombocytes (platelets), are prevented from entering the pores.

Further surprisingly, pores with an opening having a cross-sectional-dimension of about 500 nm or less have an increased sensitivity as compared to larger pores, such as pores having an opening with a cross-sectional dimension of about 800 nm or above, but having the same total pore volume/volume porosity. For example, an increase in sensitivity for absorbance measurements may be by a factor of almost two (46 µAbs/(mg Hb/dL) for 400 nm pores as compared to (25 µAbs/(mg Hb/dL)) for 800 nm pores with the same total pore volume Most preferably, the pores have a minimum opening with a respective minimum pore volume to allow for the efficient extraction of a sufficiently large subsample that can still be probed with an acceptable signal to noise ratio. Advantageously, the pores have an opening of about 30 nm or more, or 50 nm or more, or 100 nm or more, or about 200 nm or more.

Suitable pores may be produced e.g. from transparent polymer membranes with so-called track-etched pores, similar to those available from the company IT4IP (IT4IP s.a./avenue Jean-Etienne Lenoir 1/1348 Louvain-la-Neuve/Belgium) with the modification that the pores are closed at one end. Through-going pores in the membranes may be closed e.g. by laminating a backing sheet to the backside of the porous membrane, or by decelerating the ions such that the ion-bombardment tracks, and thus the pores etched following these tracks, stop within the transparent polymer membrane to form dead-end pores. The membrane is typically backed by a stiff transparent element to provide adequate mechanical strength to the translucent slab.

Further according to one embodiment of a sensor according to the invention, a porosity of a given volume of the translucent slab comprising pores is between 50% and 5% by volume, between 30% and 10% by volume, or about 15% by volume.

The pores create porosity in the translucent slab (or in a given region of the translucent slab) with a corresponding front side surface area over which the openings of the pores are distributed. The porosity may be characterized in terms of the volume of the voids created in the translucent slab by the pores, i.e. the pore volume, wherein the pore volume is referred to the volume of the translucent slab penetrated by the pores. This volume is here defined as the volume between the front side area over which the pores are distributed and the identical parallel area shifted into the translucent slab by the maximum depth of penetration of the pores into the translucent slab as seen in an axial direction perpendicular to the front side of the translucent slab.

In addition thereto, the porosity may be further characterized in terms of the integrated pore volume, which is equal to the sub-sample volume that is available for optical probing. The pore volume may conveniently be expressed as an equivalent pore volume depth DELTA, which is the pore volume referred to the corresponding front side area over which the pore openings are distributed. Accordingly, the porosity of the translucent slab can be converted into an equivalent pore volume depth DELTA as follows. The pores having an opening within a given front side area A have a total pore volume V. The equivalent pore volume depth is then calculated as the total pore volume divided by the given front side area: DELTA=V/A.

Advantageously according to some embodiments, an equivalent pore volume depth DELTA is less than 20 µm, or less than 15 µm, or less than 10 µm, or in the range from 3 µm to 5 µm, wherein the equivalent pore volume depth DELTA is defined as the total volume of the pores V divided by the front side area A over which the openings of the pores are distributed. Thereby, a small sub-sample with a representative concentration of relevant components is obtained.

A small sub-sample volume is desirable to promote a fast subsample exchange, thereby reducing response time of the sensor, and cycle time of measurements using the sensor. A small sub-sample volume is further desirable in order to avoid effects of depletion of boundary layers of the plasma fraction in the whole blood sample close to the front side of the translucent slab. Such depletion effect may otherwise occur in small, still standing samples, where e.g. red blood cells may obstruct an efficient diffusive exchange of relevant components from the volume of the whole blood sample towards the boundary layer at the front side of the translucent slab, if the equivalent pore volume depth exceeds a critical value.

Preferably, an equivalent pore volume depth DELTA is at least 1 µm, alternatively at least 2 µm, or in the range from 3 µm to 5 µm, wherein the equivalent pore volume depth is defined as above. A larger sub-sample volume is desirable to achieve a better signal-to-noise level due to a larger sub-sample volume contributing to the optically probed information on the relevant components in the plasma.

Further according to some embodiments, a useful compromise between reducing response time, reducing cycle time, and/or avoiding depletion effects in small still standing whole blood samples on the one hand, and a required or desired signal-to-noise ratio on the other hand is found for an equivalent pore volume depth DELTA in the range from 1 µm to 20 µm, preferably in the range from 2 µm to 10 µm or at about 4 µm-5 µm.

Advantageously according to one embodiment the translucent slab is supported by a translucent backing attached to the back side of the translucent slab. Thereby, an enhanced mechanical stability is achieved.

Further according to one embodiment of a sensor according to the invention, an inner wall surface of the pores is hydrophilic, e.g. coated with a hydrophilic coating. Thereby, an efficient capillary driven filling of dry pores with liquid is achieved. Furthermore, a hydrophilic coating prevents certain hydrophobic substances, such as hydrophobic dyes, hemoglobin, and other proteins, from depositing inside the pores that would otherwise lead to a gradual fouling of the sensor, which is difficult to wash out with an aqueous solution.

Further according to one embodiment of a sensor according to the invention, the light source is configured for providing an obliquely incident illuminating beam from the backside of the translucent slab, wherein an illumination angle is defined as the angle of the incident beam with respect to a surface normal of a reference plane defined by the front side of the translucent slab. Thereby, an increased optical interaction length is achieved, thus enhancing the interaction of the incident light with the content of the pores before it leaves the probing region for detection by the detector. Furthermore, penetration of probing light into the whole blood sample through the pore openings is prevented, due to a reduced apparent cross-section of the pore openings, as well as increased scattering spreading light into the probing region rather than through the pore openings into the sample space on the other side of the reflective layer.

Further according to one embodiment of a sensor according to the invention, the detector is configured to collect light obliquely emerging from the backside of the translucent slab, wherein a detection angle is defined as the angle of the propagation of the emerging light towards the detector with respect to a surface normal of a reference plane defined by the front side of the translucent slab. The detector is configured to collect light emerging in response to illumination by the light source of the optical probing arrangement.

Detecting light obliquely emerging from the backside of the translucent slab reduces contributions to the detected signal from light emerging from the whole blood sample and leaking back through the reflective layer into the probing region.

Further according to one embodiment of a sensor according to the invention, a plane of incidence and a plane of detection intersect at a surface normal to enclose an azimuthal angle of at least 0 degrees, and less than 180 degrees, preferably less than 160 degrees, preferably less than 130 degrees, or preferably about 90 degrees, wherein the plane of incidence is spanned by the direction of the illuminating beam and the surface normal to the reference plane, and wherein the plane of detection is spanned by the direction of the emerging light propagation towards the detector and the surface normal to the reference plane. Thereby, contributions to the detected signal of glare from partial reflections at optical interfaces prior to passing the probing region are reduced. Such glare of light that has not interacted with the subsample in the probing region does not comprise relevant information and is therefore detrimental to the signal-to-noise ratio.

Optical probing light may be performed by any suitable optical probing arrangement. Such optical probing arrangement may include merely directing a beam of light to the backside of the translucent slab and directing the input of an optical detector to the illuminated region. The optical arrangement may include further optical elements improving coupling of the probing light into the translucent slab and improving coupling of the light emerging from the translucent slab into the detector input. Such optical elements may include one or more prisms and/or lens arrangements attached/glued directly to the backside of the translucent slab. Preferably, the coupling optics accommodates the "reflective" nature of the optical probing, where incoming probing light and detected emerging light are kept on the same side of the reflective layer. Further improvements may be sought in enhancing the optical interaction of the probing light with the pores, e.g. by coupling the probing light into the translucent slab at a first end, forcing the light in the probing region to essentially propagate in directions parallel to the front side of the translucent slab, along the reflective surface and traversing the pores, and collecting the emerging light from another end of the translucent slab, which may be transverse or opposite of the first end.

Further according to one embodiment of a sensor according to the invention, the translucent slab is provided with further reflective elements arranged inside the pores, in a mouth portion thereof, adjacent to the opening at the front side of the translucent slab. The additional reflective elements are applied as a reflective coating on the inner wall of the pores beginning at the opening of each pore and extending into the pore. However, only a mouth portion close to the opening of the pore is covered. Providing additional reflective elements around the opening of the pores improves optical separation of the probing light from the sample chamber, thereby preventing erroneous contributions to the probed signal from red blood cells in the whole blood sample in the sample chamber. The reflecting coating may be any suitable metal coating as discussed below. The additional reflective elements may be produced in the same step as the reflective layer covering the front side of the translucent slab.

Further according to one embodiment of a sensor according to the invention, the further reflective elements are provided as a reflective coating covering only a fraction of the circumference of the mouth portion of the pores in the vicinity of the opening, wherein the fraction is about 70% or less, and preferably about 50% or less. By only partially covering the circumference of the pores a small reflector is provided in each pore with a concavely shaped reflecting surface facing towards the inside of the pores. The partial coverage may be produced, for example, by directional deposition of a metallic layer with the front side of the translucent slab inclined with respect to the direction of deposition. The openings of the pores in the plane of the front side of the translucent slab act as shadow masks. The shadow masks only allow deposition on a part of the circumferential inner wall of the pore in a mouth region thereof, i.e. close to the opening. Thereby an array of small concave mirror elements, all oriented in the same direction, may be produced.

When illuminating these small mirror elements from the concavely shaped side the resulting emerging light is directed in a preferential direction. By placing the detector in this preferential direction an improved signal-to-noise ratio is achieved as compared to other directions and as compared to embodiments without such additional small directional mirror elements.

According to some embodiments with small mirror elements, i.e. with further reflective elements having directional characteristics, an increase in intensity of the emerging light by a factor of about 3 is observed, as compared to embodiments with additional reflective elements without directional characteristics. In addition thereto, it has surprisingly been observed that a further increase by about 50% or more of the relevant signal occurs when using small mirror elements applied to the inner surface of the pores at a mouth portion thereof, e.g. when probing absorbance. This therefore results in a surprising overall improvement in S/N ratio by a factor of at least about 4 to 5.

Note that the reflecting layer at the front side of the translucent slab is still required, also when using further reflective elements, in order to ensure the optical separation of the optical probing region in the translucent slab comprising the pores from the sample chamber containing the whole blood sample. The reflective layer on the front side of the translucent slab is also necessary, e.g. for both illuminating and detecting from the back side.

Typically, the small mirror elements are symmetric with respect to a central mirror plane. Advantageously, a plane of incidence, as determined by the incident light beam, and a detection plane, as determined by the direction of detection are also arranged symmetrically with respect to this central mirror plane. According to one simplified embodiment, the plane of incidence and the plane of detection coincide, and are parallel to the central mirror planes of the small mirror elements.

Advantageously according to one embodiment the reflective layer and/or the further reflective elements are made of metal. Such metallic coatings can be applied in a relatively cost-effective, yet well-controlled manner with adequate reflectivity.

Advantageously according to one embodiment the reflective layer is made of platinum, palladium or an alloy comprising as a principal component platinum or palladium. These materials exhibit a good reflectivity in the spectral range of the electromagnetic spectrum (deep violet to blue) that is relevant for the detection of free hemoglobin, e.g. by absorbance probing. Furthermore, these materials are biocompatible and do not e.g. introduce artificial hemolysis. Furthermore, these materials are chemically stable and in the chemical environment of a whole blood sample.

Alternatively, according to some embodiments, the reflective layer may be made of silver or aluminum. Further advantageously according to some embodiments, the surfaces of the reflective layer facing towards the sample volume are encapsulated by an additional passivation layer, thereby enhancing the lifetime of the device, in particular when using silver or aluminum as a material for the reflective layer. A suitable passivation may be made of e.g. a thin layer of SiO2 which preferably is made transparent and has to be sufficiently thin so as to not obstruct the opening of the pores. These materials may also provide a good reflectivity in the relevant spectral range (red), are biocompatible and chemically stable in the environment.

Advantageously according to one embodiment, the thickness of the reflective layer is between 10 nm-100 nm depending upon the used metal. Such a layer thickness allows for applying the reflective layer by an evaporation technique without clogging of the openings of the pores at the front side of the translucent slab. At the same time, the layer thickness has to be sufficient to provide adequate attenuation of light propagating to the sample volume in order to ensure proper optical separation between the probing region and the sample volume containing the whole blood sample. Preferably, the transmitted light is less than 5%, less than 1% or even less than 0.1% in the spectral range of detection, i.e. in the spectral range from which a signal representative of the relevant plasma component is developed, such as in the range from 380 nm to 700 nm, from 380 to 450 nm, or at about 416 nm.

Advantageously according to one embodiment the detector includes a spectrophotometer and an optical probing device is configured for the spectrophotometric analysis of the light emerging from the probing region in the translucent slab. This allows for resolving the spectral signature of one or more relevant components in the light emerging from the subsample in the probing region.

Further according to a particularly advantageous embodiment, the optical probing device is configured for measuring absorbance. Thereby a surprisingly significant signal is obtained with a relatively simple optical set-up. This allows for easy integration of the sensor with more complex analysis set-ups, such as a blood analyzer system.

Advantageously according to some embodiments, the sensor or a blood analysis system comprising the sensor further comprises a processor configured for comparing the signal generated by the detector with a predetermined calibration reference to develop a quantitative measure of the free hemoglobin level in the whole blood sample.

Further advantageously according to some embodiments, the calibration reference is obtained on a dye-based calibration solution, such as an aqueous solution comprising tartrazine dye. Preferably, the dye-based aqueous solution is prepared from a typical rinse liquid with the addition of the calibrant dye, such as tartrazine.

Advantageously according to some embodiments a blood analysis system comprising the sensor further comprises an oximetry measurement system, wherein the result of the oximetry measurement system is used as an input to a processor developing a quantitative measure of the free hemoglobin level in the whole blood sample. An additional oximetry measurement system may be configured as an additional measuring cell operating in parallel or in series with a measuring cell including a free hemoglobin detector according to any of the above embodiments. The oximetry measurement typically performs the steps of hemolysing a received whole blood sample. The hemolysis may be achieved in any suitable manner, e.g. mechanical or chemically. Preferably, the hemolysis is achieved mechanically by means of ultrasound applied to the whole blood sample. The otherwise turbid whole blood sample now becomes transparent, and an absorption spectrum of the hemolysed sample is measured. From the absorption spectrum a number of parameters may be determined, which are useful as forehand information for interpreting/analyzing the signal generated by the free hemoglobin detection sensor of the invention. Operating the oximetry measurement system may thus include determining an oxigenation state, a hemoglobin-type, a bilirubin level and a presence and/or a level of any medical dyes present in the whole blood sample. The oximetry output including a determined composition and/or concentrations may then be used to correct a measurement of free hemoglobin using the sensor of the invention for interference, e.g. bilirubin interference and/or medical dyes interference. The combination of a free hemoglobin sensor with an oximetry measurement system thus allows for a more selective analysis of the detected signal, thereby improving sensitivity.

According to a further aspect of the invention a system for analyzing a whole blood sample comprises (a) a sample chamber with inlet and outlet ports for feeding and discharging the whole blood sample; (b) a first detector adapted to provide a first signal representative of a level of free hemoglobin in the whole blood sample; and (c) one or more further detectors, each further detector being adapted to provide a respective further signal representative of a blood parameter of the whole blood sample; wherein the first and further detectors are operable to obtain the first and the one or more further signals from the same whole blood sample, wherein the first detector is configured as a sensor for the optical detection of free hemoglobin according to any of the embodiments disclosed herein.

Preferably, the system for analyzing a whole blood sample comprises a processor configured to provide an additional output regarding one or more of the further signals based on the first signal. Advantageously, the additional output is a correction of the further signal with respect to the detected level of free hemoglobin, a flag indicative of a level of free hemoglobin in the whole blood sample, and/or an instruction to discard one or more of the further signals. The processor is thus adapted to correct, flag, or discard a measurement result derived from at least one of the one or more further signals on the basis of the free hemoglobin level derived from the first signal. In particular, the further signal may be indicative of any blood parameter affected by hemolysis, such as a concentration of $K^+$, $Na^+$, $Ca^{2+}$, $Mg^{2+}$, lactate dehydrogenase, iron, lipase, alpha-glutamyltransferase, creatine kinase, aspartate aminotransferase or alkaline phosphatase.

A yet further aspect of the invention relates to a porous mirror for use in the optical detection of free hemoglobin in a whole blood sample, the mirror comprising a translucent slab with a front side and a back side facing away from the front side, wherein the front side is adapted for being contacted with a whole blood sample; and a reflective layer applied to the front side of the translucent slab, the reflective layer being adapted to reflect light reaching the reflective layer from the translucent slab; wherein the translucent slab has dead-end pores penetrating the reflective layer and extending from the front side towards the backside, wherein each of the pores has a respective opening in the front side of the translucent slab, and wherein a cross-sectional dimension of the openings of the pores is dimensioned so as to prevent red blood cells from entering the pores, while allowing hemoglobin to enter the pores.

As already discussed above, by this design it is achieved that the pores can be filled from the front side with a subsample comprising relevant components of the plasma in representative amounts, merely by contacting the front side surface of the porous mirror with a whole blood sample, and that the subsample thus extracted can conveniently be optically probed separate from the whole blood sample. Relevant components are substances that are present in the plasma phase of the whole blood sample and that are to be measured/detected using the sensor. A representative subsample of the plasma phase may be extracted from the whole blood sample and transferred into the pores by means of diffusion and/or capillary forces. As also discussed above, the pores are preferably prefilled with a liquid that is compatible with the plasma phase, such as an aqueous solution commonly used for rinse, calibration and/or quality control purposes in blood analyzers. Non-limiting examples of suitable solutions are given further below. Priming the pores with such a known liquid allows for extracting a subsample representative of the relevant components in the plasma into the pores by diffusion alone.

Advantageously according to an aspect of the invention, a method of optically detecting free hemoglobin in a whole blood sample is provided as detailed in the following. The method at least achieves the same advantages as discussed above with respect to respective embodiments of a sensor for detecting free hemoglobin, or of a system comprising such a sensor.

According to some embodiments, a method of optically detecting free hemoglobin in a whole blood sample comprises the steps of providing a porous mirror as disclosed above; contacting the porous mirror with a reference liquid so as to fill the pores with the reference liquid; contacting the front side of the porous mirror with a whole blood sample; waiting for a diffusion time to allow for diffusion of components in the plasma from the sample chamber into the pores to stabilize; optically probing the liquid inside the pores, from the side of the reflective layer facing away from the sample chamber; and, based on the result of the optical probing, establishing a free hemoglobin level of the whole blood sample. Preferably, the reference liquid is an aqueous solution that is compatible with the whole blood sample, and in particular with the plasma fraction thereof, such as a liquid for rinse, calibration and/or quality control. In some embodiments, it may be conceived to omit the step of contacting the front side of the mirror with a reference liquid prior to introducing the whole blood sample. However, including the step allows for a purely diffusive sub-sample extraction, which is very efficient and leads to a surprisingly fast detection response and surprisingly short cycle time for the measurement. Most advantageously, free hemoglobin is detected optically in the pores by the color change due to the presence of free hemoglobin in representative amounts in the extracted subsample.

Advantageously according to some embodiments, optical probing comprises illuminating the translucent slab with probing light from the backside and performing a spectrophotometric analysis of the light emerging from the backside of the translucent slab as an optical response to the probing light.

Advantageously according to some embodiments, optical probing is measuring the absorbance.

Advantageously according to some embodiments the method further comprises the step of comparing the optical response with a predetermined calibration reference to develop a quantitative measure of the free hemoglobin level in the whole blood sample.

Further advantageously according to some embodiments of the method, the calibration reference is obtained on a dye-based calibration solution, such as an aqueous solution comprising tartrazine dye. Preferably, the dye-based aqueous solution is prepared from a typical rinse liquid with the addition of the calibrant dye, such as tartrazine.

Further advantageously, an aspect of the invention relates to a method of analyzing a whole blood sample, wherein the method comprises optically probing a free hemoglobin level of the whole blood sample as disclosed above; on the same whole blood sample, measuring a further component present in the whole blood sample;

and correcting flagging or discarding the measurement of the further component on the basis of the hemolysis level of the whole blood sample.

BRIEF DESCRIPTION OF THE DRAWINGS

Preferred embodiments of the invention will be described in more detail in connection with the appended drawings, which show in FIG. 1 schematically, a sensor device according to one embodiment, under operational conditions, FIG. 2 schematically, a cross-sectional detail of a pore, with an additional reflecting element, according to one embodiment;

FIGS. 3*a/b* schematically, two cross-sectional side views of a detail of a pore, with an additional reflecting element, according to a further embodiment;

DETAILED DESCRIPTION OF PREFERRED EMBODIMENTS

Figure 4:
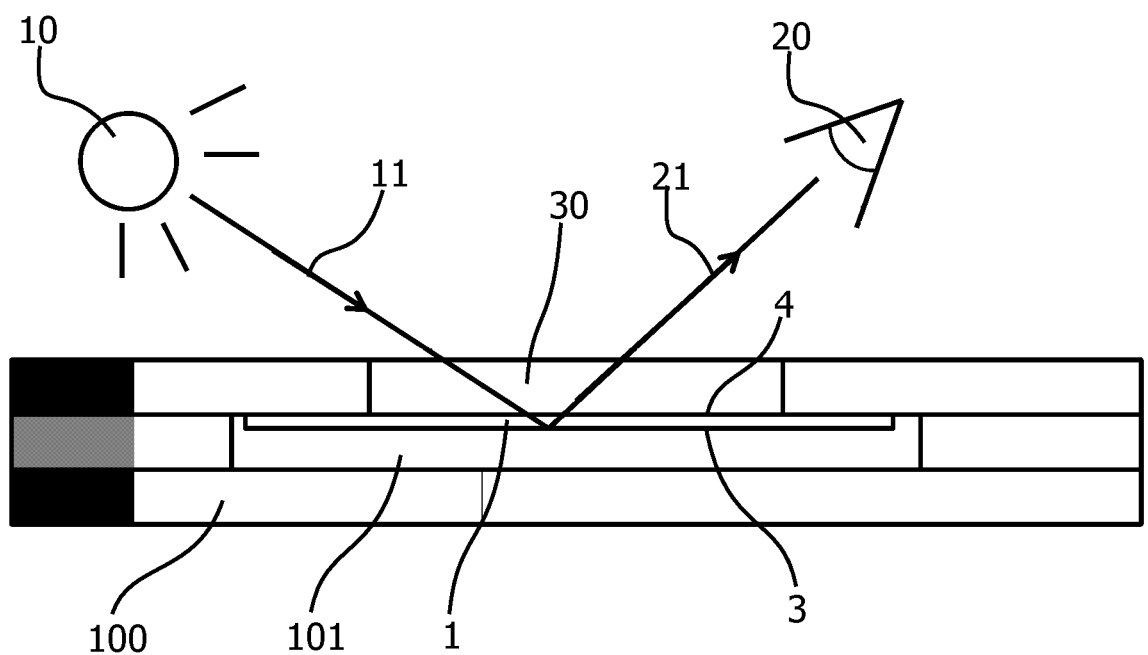
FIG. 4 schematically, a cross-sectional side view of a measurement cell.

FIG. 1 shows schematically, a cross-sectional view of a porous mirror 1 operated in a sensor device according to one embodiment. The porous mirror 1 comprises a translucent slab 2, with a front side 3 and a back side 4. The front side 3 is provided with a reflective layer 5. The translucent slab 2 further comprises dead-end pores 6 extending from an opening 7 at the front side 3 through the reflective layer 5 into the bulk of the translucent slab 2, where they terminate. While shown like that in the schematic drawing of FIG. 1, the pores do not have to be perpendicular to the front side 3 or parallel to each other. Under operation, the front side 3 of the porous mirror with pore openings 7 is contacted with a whole blood sample 99. The whole blood sample has a cellular fraction comprising red blood cells 98, and a plasma fraction 97 with relevant components to be detected, here free hemoglobin 96. A cross-sectional dimension of the openings 7 of the pores 6 is dimensioned so as to prevent red blood cells 98 from entering the pores 6, while allowing hemoglobin 96 to enter the pores 6.

The pores 6 may be pre-filled with a rinse solution 8 that is compatible with the whole blood sample 99, and in particular with the plasma fraction 97. When the whole blood sample 99 contacts the front side 3 of the porous mirror 1 with the pre-filled pores 6, a diffusive transfer of the free hemoglobin 96 into the pores 6 occurs, thereby establishing a sub-sample inside the pores 6 with a concentration of free hemoglobin 96 that is representative of the concentration of free hemoglobin 96 in the whole blood sample 99.

The rinse solution 8 used for pre-filling the pores 6 may be any aqueous solution compatible with the whole blood sample 99. Suitable rinse solutions include those commonly used for rinse, calibration, and/or quality control purposes in blood parameter analyzers. Such solution compositions typically include organic buffers, inorganic salts, surfactant, preservatives, anti-coagulant, enzyme, colorant and sometimes metabolites. This provides the following substances with approximate concentrations as given in Table 1 below.

TABLE 1

| Substance | Unit | Concentration | | |
|---|---|---|---|---|
| | | CAL1 S1920 | CAL2 S1930 | CAL3 S1940 |
| pH | | 7.30 | 6.8 | NA |
| $pCO_2$ | mmHg | 35 | NA | 80 |
| $pO_2$ | mmHg | 180 | NA | NA |
| $cNa^+$ | mmol/L | 150 | 70 | NA |
| $cK^+$ | mmol/L | 4 | 10 | NA |
| $cCl^-$ | mmol/L | 95 | 50 | NA |
| $cCa^{2+}$ | mmol/L | 0.5 | 2.3 | NA |
| cGlu | mmol/L | 0 | NA | 10 |
| cLac | mmol/L | 0 | NA | 10 |
| ctHb | g/dL | NA | NA | 0 |

Optical detection is performed from the backside using an optical probing arrangement with a light source 10 and a detector 20. The light source 10 illuminates a probing volume in the porous portion of the translucent slab 2 from the side of the reflective layer 5 facing away from the whole blood sample 99. The probing light 11 is an obliquely incident beam interacting with the subsample 9 in the pores 6. Emerging light 21 is detected by the detector 20 also arranged to view the probing region at an oblique angle. The detector 20 generates a signal representative of the emerging light, and in particular contains information on the concentration of free hemoglobin 96, due to the interaction with the subsample 9 in the pores 6. Processing the generated signal allows developing a level of free hemoglobin in the whole blood sample. Using calibration, the level of free hemoglobin in the whole blood sample may be quantitative. The optical probing technique used for all measurements in the examples below uses spectrally resolved absorbance measurements in the visible range of the electromagnetic spectrum, e.g. with wavelengths in the range between about 380 nm and 700 nm, between about 380 nm and 450 nm, or at about 416 nm.

A measurement cycle is concluded by washing out the whole blood sample with a rinse solution, such as the rinse solution 8 used for pre-filling the pores 6. Thereby, the sensor device is re-initialized and ready for receiving the next whole blood sample. By way of example, Table 2 gives an indication of the very fast recovery after exposure to a test sample comprising 5% of fully hemolysed whole blood, i.e. about 1000 mg/dL).

TABLE 2

| Washout | Sensor 1 Signal (mg Hb/dL) | Sensor 2 Signal (mg Hb/dL) |
|---|---|---|
| 5.0% HWB (~1000 mg/dL) | 973 | 1016 |
| Rinse 1 min. after | −2 | −11 |
| Rinse 2 min. after | 5 | −10 |
| Rinse 3 min. after | 0 | 0 |

From table 2 it can be seen that a measuring cell comprising two sensors (sensor 1 and sensor 2 as also referred to in the examples below) fully recovers after measuring a sample with a particularly high concentration of free hemoglobin of 1000 mg/mL, and is ready for receiving the next sample within 1 minute after initiating a rinse, or even faster.

FIG. 2 shows a detail of a porous mirror according to a further embodiment. A single pore 6 in the translucent slab 2 is shown schematically. The pore 6 comprises an additional reflective element in the form of a reflective collar 51 produced by a deposition of reflective material into a mouth portion at the opening 7 of the pore 6.

FIG. 3a and FIG. 3b show two cross-sectional views of a detail of a porous mirror according to yet a further embodiment. Again, a single pore 6 in the translucent slab 2 is shown schematically. The pore 6 comprises an additional reflective element in the form of a small mirror element 52 produced by a directional deposition of reflective material into the mouth portion at the opening 7 of the pore 6, wherein the mirror only covers a fraction of the circumference of the opening/mouth portion as indicated in the two views of FIGS. 3a,b. The small mirror element 52 is concave as seen from the inside of the pore. By producing the small mirror elements with directional evaporation of a suitable reflective material, preferably metal, onto an inclined porous translucent slab 2, all mirror elements 52 are formed at the same time and pointing in the same direction. Thereby, a preferential direction of the emerging light 21 is achieved when probing light 11 is incident from the concave side of the small mirror elements 52. Consequently, the signal-to-noise ratio of a signal generated from light emerging in the preferential direction is improved considerably.

All examples given below have been measured using a sensor configuration with additional small mirror elements as obtained by a directional sputter evaporation of Pd onto the front side of a translucent polymer slab 2 with a direction of evaporation at an angle of inclination of 25 degrees with respect to the surface normal on the front side 3, until a reflective layer 5 with a thickness of 30 nm on the front side 3 of the translucent slab 2 is obtained. The translucent slab 2 is made of a translucent, preferably transparent, polymer material and has track-etched dead-end pores 6 with an essentially circular cross-section. The pores have an opening 7 with a diameter of 400 nm and a depth of 25 µm distributed with a porosity of 15% by volume. Together, the pores distributed over a given front side surface area A have a total volume V and have an equivalent pore volume depth DELTA=V/A. For the above specified sample used for measurements in the examples given below, the equivalent pore volume depth DELTA is about 4 µm.

Figure 5:
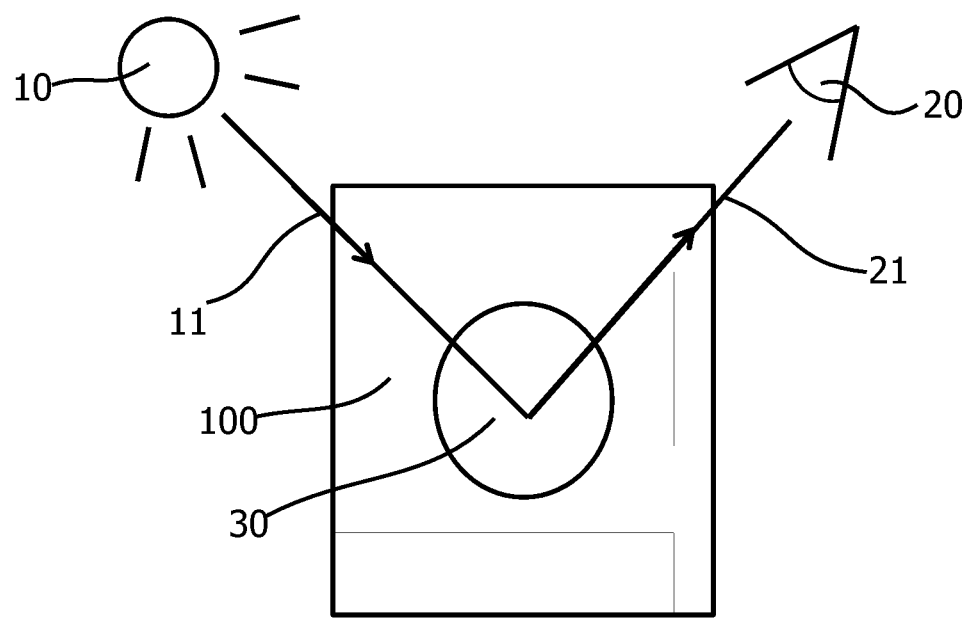
FIG. 5 a top elevational view of the measurement cell of FIG. 4.

FIG. 4 and FIG. 5 show schematically a measurement cell 100 comprising a sensor device with a porous mirror 1 with its front side 3 with pore openings 7 facing into a sample volume 101 inside the measurement cell 100. The sample volume communicates with fluid input and output ports (not shown) for feeding and discharging samples and for performing priming, rinsing, and wash-out steps. The back side of the porous mirror is mechanically stabilized by a transparent backing slide 30, which also acts as a window for optical access to the probing region from the back side 4 of the porous mirror. Optical probing is performed using an arrangement with a light source 10 and a detector 20 as described above with reference to FIG. 1, wherein the probing beam and the direction of detection are inclined with respective angles to a surface normal on the plane of the front side 3 of the porous mirror 1. Furthermore, as best seen in FIG. 5, the planes of incident probing light 11 and of detection 21 preferably intersect each other with an angle of less than 180 degrees to avoid glare effects, and preferably at a pointed angle of about 90 degrees or below. In the measurements of the examples given below, the planes of incident probing light 11 and of detection of emerging light 21 are arranged symmetrically with respect to a direction parallel to the symmetry planes of the small mirror elements 52.

Figure 6A:
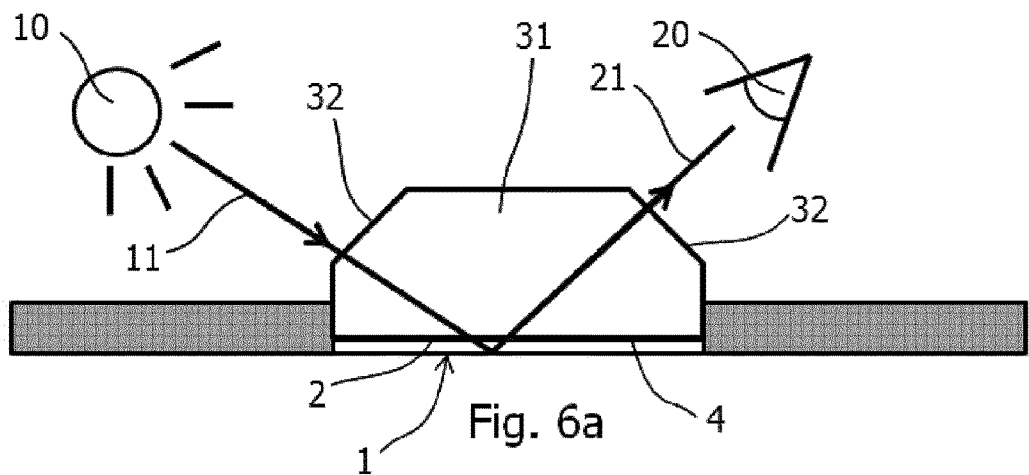
FIGS. 6*a/b* schematically, two cross-sectional side views of a measurement cell with prism-like outside of the transparent backing, according to a further embodiment.
Figure 6B:
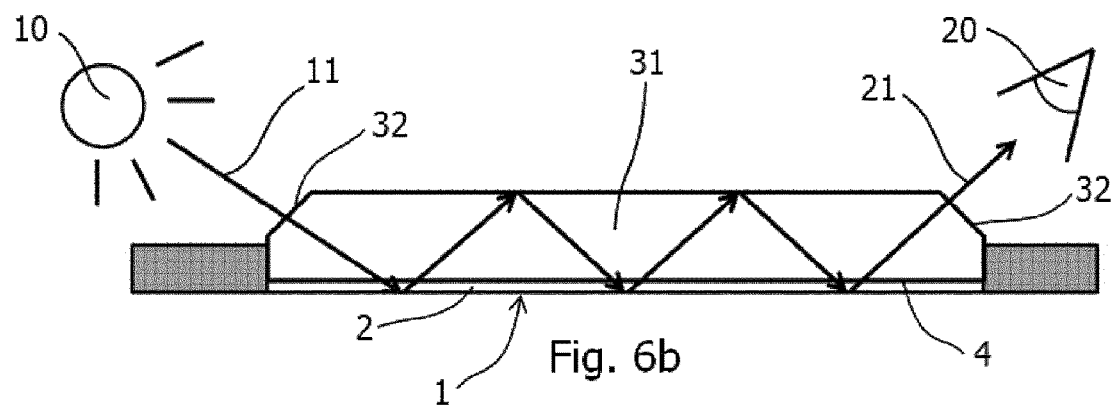
Figure 7:
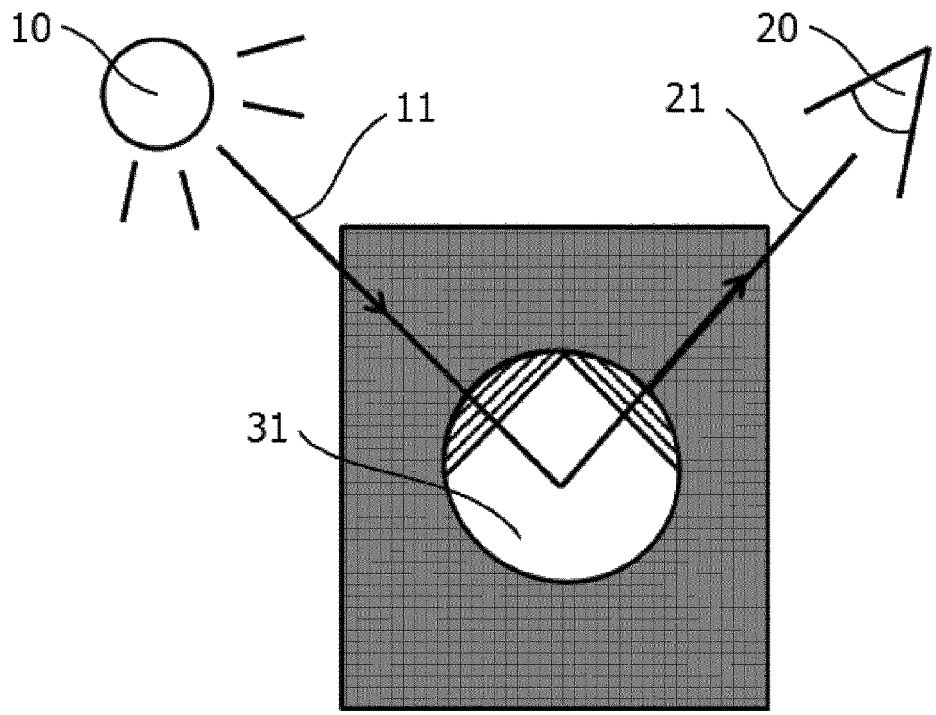
FIG. 7 a top elevational view of the measurement cell of FIG. 6*a;*

FIG. 6a, 6b and FIG. 7 show schematically a transparent backing slide 31 in direct contact with the back side 4 of the translucent slab 2 of the porous mirror 1. When incident probing light 11 enters the back slide 4 of the translucent slab 2 with the surface at 60° prism 32, the shift in refractive index between air and polymer does not affect the incident probing light 11 and the light enter the pores 6 (not seen) of the translucent slab 2 without change of the angle of the light and the emerging light 21 reaches the detector 20. FIG. 6b shows that the incident probing light 11 may be reflected several times in the transparent backing slide 31 before the emerging light 21 reaches the detector 20. Furthermore, as best seen in FIG. 7, the planes of incident probing light 11 and the emerging light 21 preferably intersect each other with an angle of less than 180 degrees to avoid glare effects, and preferably at a pointed angle of about 90 degrees or below and the prisms 32 does not affect the incident probing light 11, nor the emerging light 21.

Examples

Referring to FIGS. 8-13 in the following, data from test run measurements are given as examples illustrating different aspects of the performance of a sensor according to an embodiment of the invention.

The sensor use for the experiments of these examples where produced from a transparent PETP-membrane, with a total thickness 49 µm that is provided with single-sided track-etched, linear pores. The pores have a pore depth of 25 µm and a pore diameter of 0.4 µm with a hydrophilic PVP treatment. The areal pore density is 1.2E8/cm^2. The pores are thus dead-end with an opening at one side of the PETP-membrane, ending essentially half way into the PETP-membrane acting as the translucent slab. The porous side of the membrane (translucent slab) is sputter coated with Palladium at an angle of 25 degrees and with an approximate layer thickness of 30 nm. This gives a metal coating on the porous front-side of the membrane (translucent slab) and a small coating on one side of the inside of the pores thus forming small concave mirrors in a mouth portion of the pores adjacent to their opening towards the front side. The sputtered porous PETP-membrane is laminated to a custom build cuvette using a double sided adhesive tape so that the concave side of the small mirrors in the pores is pointing halfway between light guides from the light source and from a spectrometer input. A drop of approximately 10 µL of silicon rubber is pipetted onto the membrane and a cover glass is then fixed to the backside of the membrane as a mechanical backing of the sensor membrane (translucent slab). The sensor is mounted in a test bench for automatic handling of liquids, time intervals and data sampling. Data acquisition last approximately 3 s and is delayed until 14 s after sample acquisition.

The test bench is equipped with two light emitting diodes (a purple and a 'white' LED) as light source, and with a mini-spectrometer as a detector. The standard slit in the mini-spectrometer has been replaced with a 125 µm slit in order to increase light and sensitivity. As the measurement is a reflection measurement, the light source and detector are both placed on the back side (none porous side) of the porous membrane. The porous metal coated side of the membrane is positioned on the inside of the measuring chamber and the mirror and the pores are thus directly exposed to the samples in the chamber. Light from the two light diodes are led through a common fiber light guide, which has a lens at the end for collimating the light to a small spot of the porous mirror membrane (approximately 2 mm by 2 mm). Referring to a Cartesian coordinate system, the plane of the membrane (front side of the translucent slab) may be defined as the ZX-plane of the coordinate system. The light enters the membrane outer surface (back side of the translucent slab) at a 45° angle with respect to the Y-axis, i.e. the surface normal to the ZX-plane (and in the YZ-plane of the coordinate system). The detector is positioned with a polar angle of 60° with respect to the Y-axis, and turned with respect to the YZ-plane by an azimuthal angle of 90° with respect to the plane of incidence of the light source (e.g. in the YX-plane). The relatively high angles of light incidence and detection direction with respect to the Y-axis results in improved detection sensitivity for hemoglobin, since the collected light has traveled through a greater length of the sub-sample in the pores.

Samples are prepared by mixing hemolysed and un-hemolysed human blood in the specified mixing ratios. The hemolysed blood is prepared by freezing for 30 minutes at −80° C. The interference solutions based on plasma are prepared by spiking the plasma with interferents to the specified values. Plasma is produced by centrifugation in 15 min. at 1500 G. As reference, the absorbance spectra of centrifugation derived plasma from all whole blood samples tested are also measured on a Perkin Elmer Lambda 19 UV-Vis spectrometer.

Figure 8:
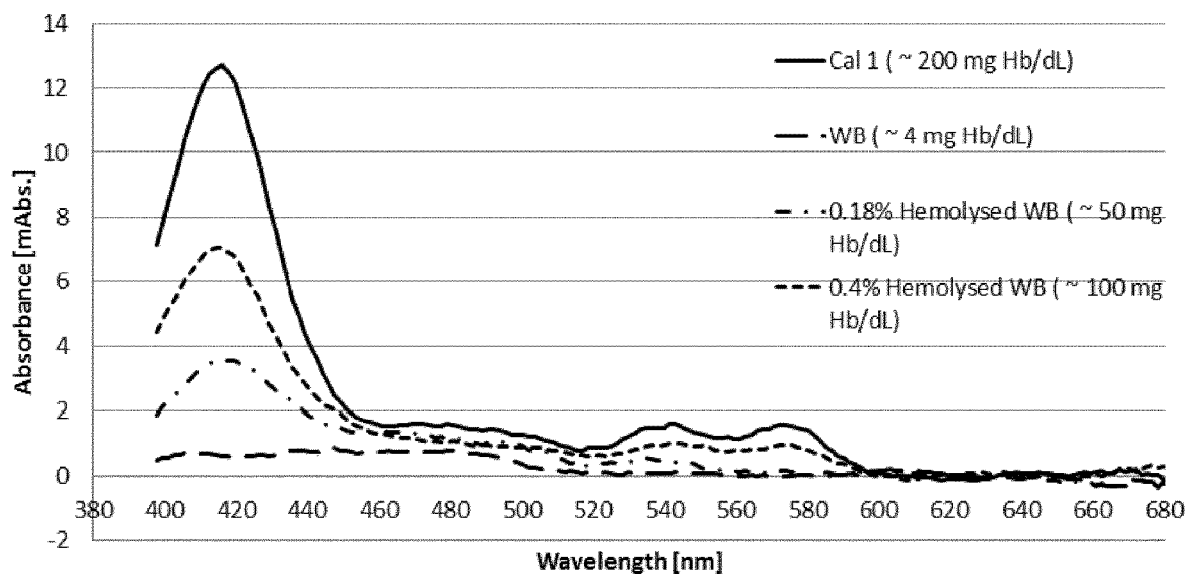
FIG. 8 a graph showing examples of absorbance spectra for samples with different content of free hemoglobin.

Spectral FIG. 8 shows spectrally resolved absorbance data for four samples with different concentrations of free hemoglobin (Hb). At a wavelength of around 416 nm a pronounced peak is observed wherein the absorbance maximum for the different samples evidently scales linearly according to their content in free hemoglobin. Picking the absorbance traces from top to bottom at the peak at 416 nm, the samples have nominal concentrations of 200 mg Hb/dL (Cal 1), 100 mg Hb/dL (0.4% hemolysed whole blood), 50 mg Hb/dL (0.18% hemolysed whole blood), and about 4 mg Hb/dL (whole blood).

Figure 9:
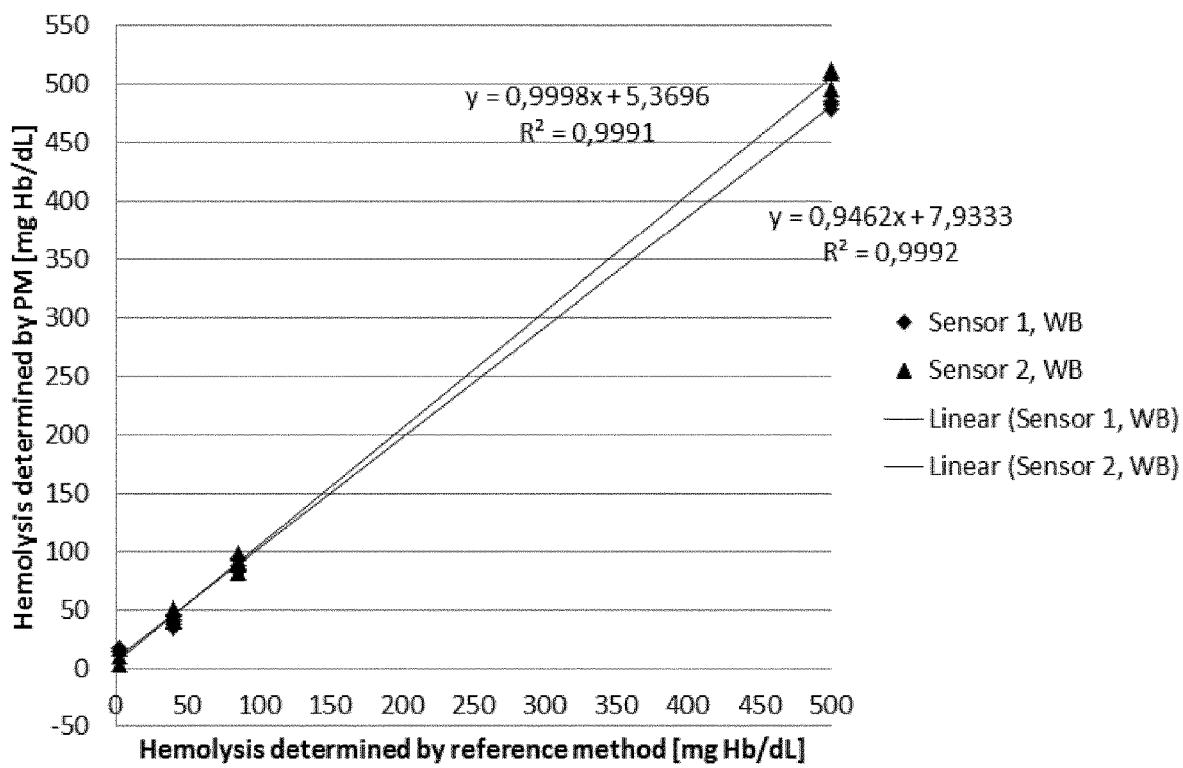
FIG. 9 a graph showing examples of free hemoglobin measurements obtained using a sensor according to one embodiment of the invention as compared to measurements using a reference method.

The linear scaling and correct calibration of the values for the free hemoglobin content as obtained by optical sensors with a porous mirror (sensor 1, sensor 2) has been verified by measuring the same samples using a reference method (FIG. 9). The reference method involves separating the plasma fraction from the cellular fraction of the whole blood by centrifuging, and determining the respective concentrations of free hemoglobin by performing a spectrophotometry measurement on the isolated plasma phase. The spectrophotometry technique of reference was also a spectrally absorbance measurement obtained using a PerkinElmer Lambda 19 UV-Vis spectrometer. Independent measurements obtained using two nominally identical sensor devices, named sensor 1 and sensor 2 are shown to largely coincide. Respective linear trendlines for each of the sensors have been added to the graph. The trendlines underline the high precision and reliability of the free hemoglobin concentration values as obtained using the sensors 1 and 2 according to the invention.

Figure 10:
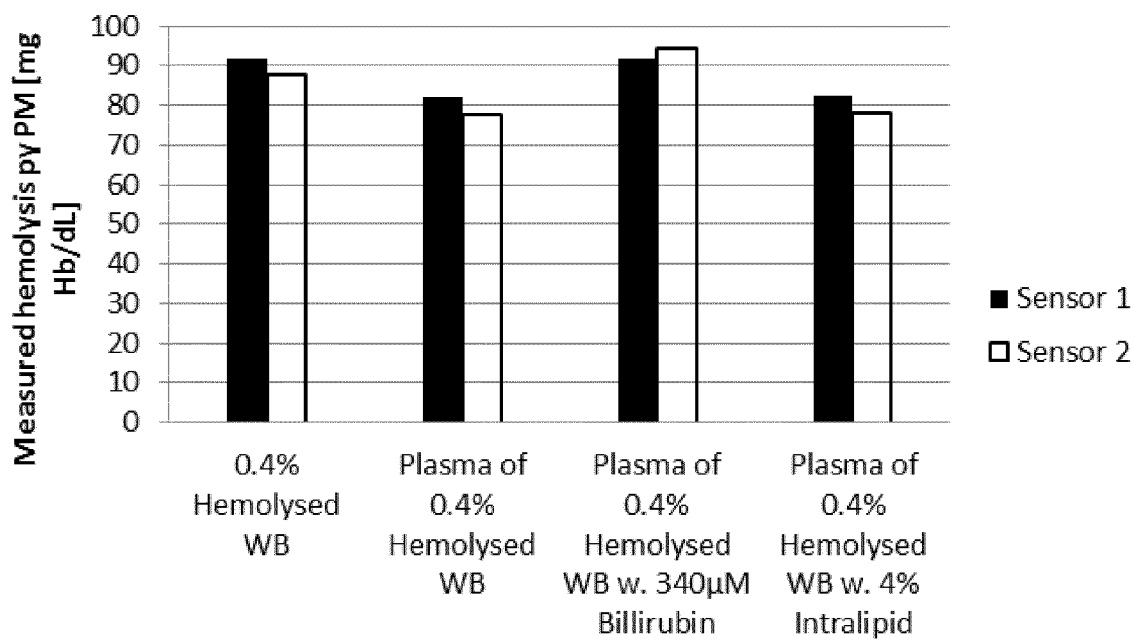
FIG. 10 a graph showing examples of response to interference substances.

FIG. 10 illustrates the robustness of the free hemoglobin measurements as obtained using a sensor according to the invention against interference from other components that may be present in the plasma. Again, data from both sensor 1 (solid columns) and sensor 2 (open columns) are shown side by side. From left to right, the four different samples measured for determining interference are 0.4% hemolysed whole blood (first group of columns), centrifugation derived plasma of the 0.4% hemolysed whole blood (second group of columns), the centrifugation derived plasma of 0.4% hemolysed whole blood with 340 µM bilirubin added (third group of columns), and the centrifugation derived plasma of 0.4% hemolysed whole blood with 4% intralipids added (fourth group of columns). All signals show a content of free hemoglobin between 77 and 93 mg Hb/dL as measured using a porous mirror sensor (sensors 1 and 2). For reference, a signal measured on the centrifugation derived plasma of 0.4% hemolysed whole blood yields a content of about 85 mg Hb/dL when using the above described reference method (not shown). A comparison of the first and second groups of columns shows a minor, but insignificant contribution from red blood cells to the hemoglobin signal. A comparison of the second and third groups of columns shows a noticeable, but insignificant interference of bilirubin signal with the hemoglobin signal. A comparison of the second and fourth groups of columns shows no detectable interference of the hemoglobin signal with any intralipid signal.

Figure 11:
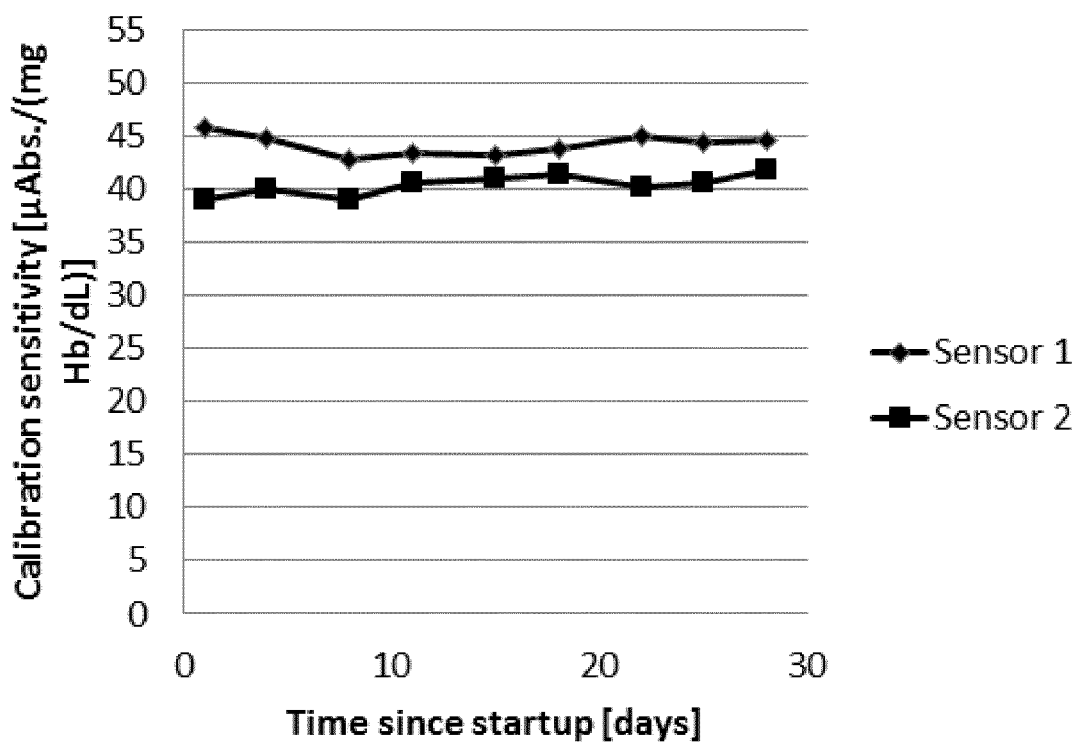
FIG. 11 a graph giving examples of the stability of the calibration sensitivity over a longer period.

FIG. 11 shows measurements on nominally identical samples repeated over a longer period of one month. No significant variation in the signal sensitivity as determined by the absorbance per mg Hb/dL is observed. Accordingly, the sensor using a porous mirror yields a highly stable and reproducible results.

Figure 12:
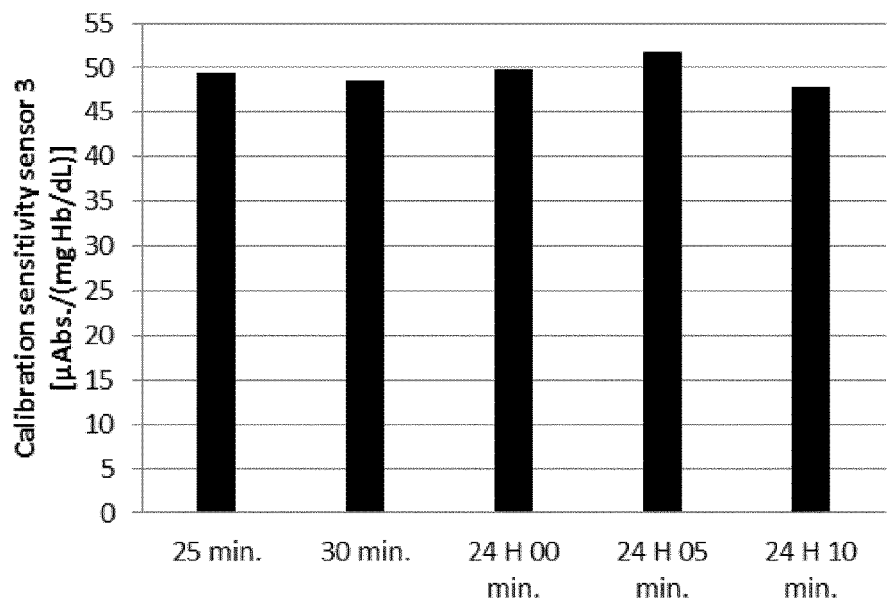
FIG. 12 a graph showing the dynamics of the calibration sensitivity in a start-up phase of the detector; and in FIG. 13 a graph showing an example of using a dye as a calibration and quality control reference for spectrophotometric measurements.

FIG. 12 shows results from the same type of measurements, however performed over a relatively short period, thereby illustrating the start-up dynamics of a virgin sensor. No significant variation is observed over the entire period. Already within 3 minutes since the first wetting of the sensor porous surface, a stable and reproducible signal is observed, thus illustrating a prompt response with no significant start-up delay.

Figure 13:
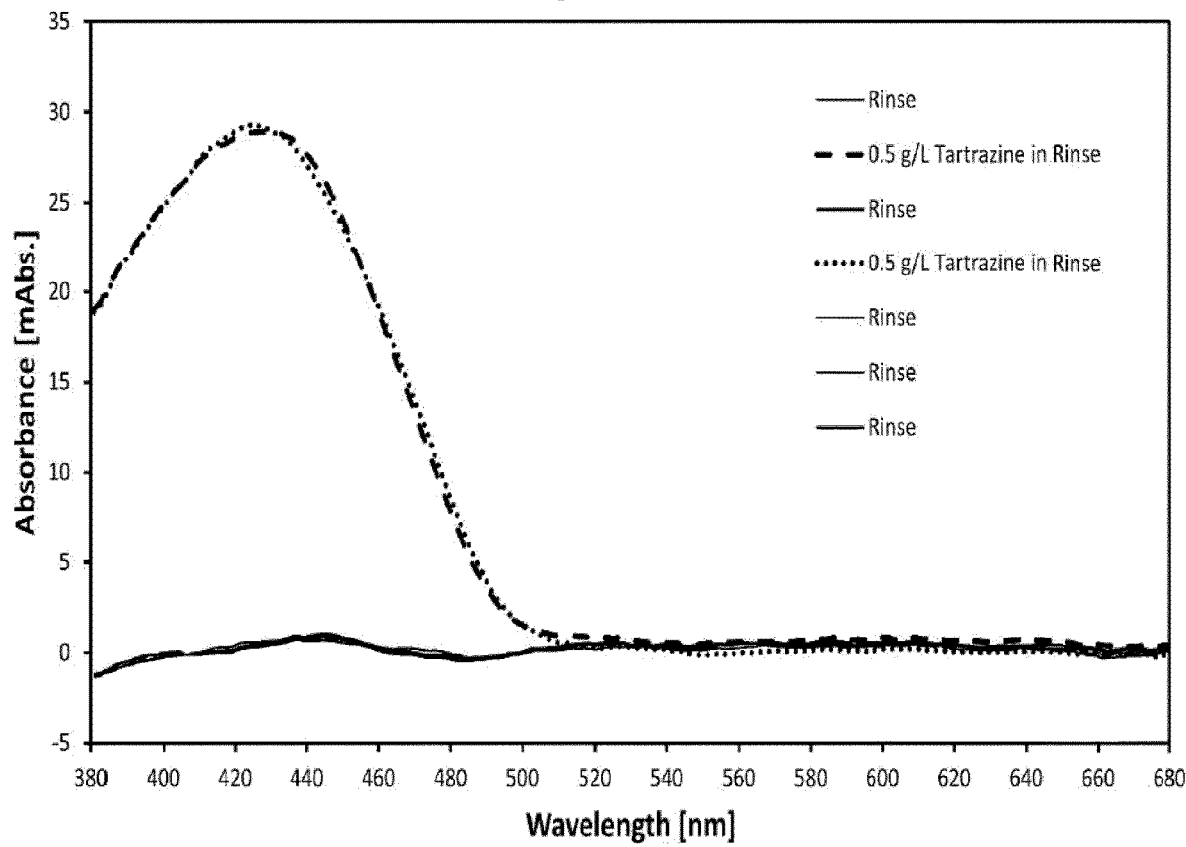

FIG. 13 shows an example with a series of spectrally resolved absorbance data obtained on a dye-based calibration solution and, for comparison, on a rinse solution. The spectra where obtained in successive cycles immediately after each other. The dye-based calibration solution is a rinse solution with an addition of 0.5 g tartrazine per 1 L rinse. The sequence of measured solutions is as follows: First a rinse solution, then a dye-based calibration solution, then again a rinse solution, again the same dye-based solution and a sequence of three consecutive measurements all performed on rinse solution. All spectra are plotted on the same scale and on top of each other. The experiment shows again a very good stability and reproducibility of the obtained results. Yet more important, the data shows a surprisingly clear separation of the two dye-based solution spectra coinciding on top of each other, and all five rinse solution spectra also coinciding on top of each other. Note that the optical data are all probed in the probing volume of the porous mirror sensor. This indicates a very efficient and complete diffusive exchange for extraction and washout of the subsample in the pores also when using a dye-based spectrophotometric calibration solution, such as the above-mentioned tartrazine dyed rinse solution.

While the device and method of the invention has been discussed specifically with reference to the detection of free hemoglobin, according to a broader aspect, the devices and methods discussed herein are equally applicable to the detection of other optically active substances in the plasma fraction of a whole blood sample, wherein "the term optically active" refers to substances, that can be detected directly by a spectroscopic optical probing technique. Such substances may include, but are not limited to metabolic substances, pharmaceutical substances, drugs, or vitamins.

The invention claimed is:

1. A sensor for the optical detection of a substance in the plasma fraction of a whole blood sample, the sensor comprising:
   a translucent slab with a front side and a back side facing away from the front side, wherein the front side is adapted for being contacted with a whole blood sample, wherein the translucent slab comprises pores;
   a reflective layer at the front side of the translucent slab, the reflective layer being adapted to reflect light reaching the reflective layer from the translucent slab; and
   a light source and a detector configured for optically probing the translucent slab, wherein the light source is adapted to illuminate at least the pores in the translucent slab, wherein the detector is arranged to receive light emerging from the pores in response to an illumination by the light source, and wherein the detector is adapted to generate a signal representative of the detected light;
   wherein the pores in the translucent slab are dead-end pores extending from respective openings at the front side, through the reflective layer into the translucent slab, wherein a cross-sectional dimension of the openings of the pores is dimensioned so as to prevent red blood cells from entering the pores, while allowing the substance in the plasma fraction of the whole blood sample to enter the pores.

2. The sensor according to claim 1, wherein the sensor is adapted for the optical detection of free hemoglobin in a whole blood sample, wherein a cross-sectional dimension of the openings of the pores is dimensioned so as to prevent red blood cells from entering the pores, while allowing free hemoglobin to enter the pores.

3. The sensor according to claim 1, wherein a cross-sectional dimension of the openings of the pores is about 1 µm or less, about 800 nm or less, about 500 nm or less, or about 400 nm or less, and/or wherein a length of the pores in an axial direction along the pores is less than 100 µm, less than 50 µm, less than 30 µm, or about 25 µm.

4. The sensor according to claim 1, wherein a porosity of a given volume of the translucent slab comprising pores is between 50% and 5% by volume, between 30% and 10% by volume, or about 15% by volume.

5. The sensor according to claim 1, wherein an equivalent pore volume depth (DELTA) is less than 20 µm, less than 10

µm, or about 5 µm or less, wherein the equivalent pore volume depth (DELTA) is defined as the total volume of the pores (V) divided by the front side area (A) over which the openings of the pores are distributed.

6. The sensor according to claim 1, wherein an inner wall surface of the pores is coated with a hydrophilic coating.

7. The sensor according to claim 1, wherein the light source is configured for providing an obliquely incident illuminating beam from the backside of the translucent slab, wherein an illumination angle is defined as the angle of the incident beam with respect to a surface normal of a reference plane defined by the front side of the translucent slab.

8. The sensor according to claim 1, wherein the detector is configured to collect light obliquely emerging from the backside of the translucent slab, wherein a detection angle is defined as the angle of the propagation of the emerging light towards the detector with respect to a surface normal of a reference plane defined by the front side of the translucent slab.

9. The sensor according to claim 8, wherein a plane of incidence and a plane of detection intersect at a surface normal to enclose an azimuthal angle of at least 0 degrees and less than 180 degrees, less than 160 degrees, less than 130 degrees, or about 90 degrees, wherein the plane of incidence is spanned by the direction of the illuminating beam and the surface normal to the reference plane, and wherein the plane of detection is spanned by the direction of the emerging light propagation towards the detector and the surface normal to the reference plane.

10. The sensor according to claim 1, wherein the translucent slab is provided with further reflective elements arranged inside the pores, in a mouth portion thereof, adjacent to the opening at the front side of the translucent slab.

11. The sensor according to claim 10, wherein the further reflective elements are provided as a reflective coating covering only a fraction of the circumference of the mouth portion of the pores in the vicinity of the opening, wherein the fraction is about 70% or less or about 50% or less.

12. A system for analyzing a whole blood sample, the system comprising
a sample chamber with inlet and outlet ports for feeding and discharging the whole blood sample;
a first detector adapted to provide a first signal representative of a level of a substance in a plasma phase of the whole blood sample; and
one or more further detectors, each further detector being adapted to provide a respective further signal representative of a blood parameter of the whole blood sample;
wherein the first and further detectors are operable to obtain the first and the one or more further signals from the same whole blood sample, wherein the first detector is configured as a sensor for the optical detection of the substance in the plasma phase of the whole blood sample according to claim 1.

13. The system according to claim 12, further comprising a processor configured to provide an output regarding one or more of the further signals based on the first signal.

14. The system according to claim 13, wherein the output is a correction of the further signal with respect to a detected level of free hemoglobin, a flag indicative of a level of free hemoglobin in the whole blood sample, and/or an instruction to discard one or more of the further signals.

15. A porous mirror for use in the optical detection of free hemoglobin in a whole blood sample, the porous mirror comprising:
a translucent slab with a front side and a back side facing away from the front side, wherein the front side is adapted for being contacted with a whole blood sample; and
a reflective layer applied to the front side of the translucent slab, the reflective layer being adapted to reflect light reaching the reflective layer from the translucent slab;
wherein the translucent slab is provided with dead-end pores extending from respective openings at the front side into the translucent slab, wherein a cross-sectional dimension of the openings of the pores is dimensioned so as to prevent red blood cells from entering the pores, while allowing free hemoglobin to enter the pores.

16. A sensor for the optical detection of a substance in the plasma fraction of a whole blood sample, the sensor comprising:
a translucent article comprising (a) at least one membrane comprising pores and (b) a transparent element with a front side and a back side facing away from the front side, wherein the front side is adapted for being contacted with a whole blood sample;
a reflective layer at the front side of the translucent article, the reflective layer being adapted to reflect light reaching the reflective layer from the translucent article; and
a light source and a detector configured for optically probing the translucent article, wherein the light source is adapted to illuminate at least the pores in the translucent article, wherein the detector is arranged to receive light emerging from the pores in response to an illumination by the light source, and wherein the detector is adapted to generate a signal representative of the detected light;
wherein the pores in the translucent article are dead-end pores extending from respective openings at the front side, through the reflective layer into the at least one membrane, wherein the pores are only in fluid communication with the sample at the front side of the at least one membrane, wherein a cross-sectional dimension of the openings of the pores is dimensioned so as to prevent red blood cells from entering the pores, while allowing the substance in the plasma fraction of the whole blood sample to enter the pores.

17. The sensor according to claim 16, wherein an inner wall surface of the pores is coated with a hydrophilic coating.

* * * * *